United States Patent
Meltsner (10) Patent No.: US 11,471,702 B2
(45) Date of Patent: Oct. 18, 2022

(54) RAY TRACING FOR A DETECTION AND AVOIDANCE OF COLLISIONS BETWEEN RADIOTHERAPY DEVICES AND PATIENT

(71) Applicant: KONINKLIJKE PHILIPS N.V., Eindhoven (NL)

(72) Inventor: Michael Adam Meltsner, Durham, NC (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/470,475

(22) PCT Filed: Dec. 19, 2017

(86) PCT No.: PCT/EP2017/083656
§ 371 (c)(1),
(2) Date: Jun. 17, 2019

(87) PCT Pub. No.: WO2018/115022
PCT Pub. Date: Jun. 28, 2018

(65) Prior Publication Data
US 2019/0329073 A1    Oct. 31, 2019

Related U.S. Application Data

(60) Provisional application No. 62/438,504, filed on Dec. 23, 2016.

(51) Int. Cl.
*A61N 5/10* (2006.01)
*A61B 6/10* (2006.01)
*G16H 20/40* (2018.01)

(52) U.S. Cl.
CPC .............. *A61N 5/103* (2013.01); *A61B 6/102* (2013.01); *A61N 5/10* (2013.01); *A61N 5/1031* (2013.01);
(Continued)

(58) Field of Classification Search
CPC .......... A61B 6/102; A61N 5/10; A61N 5/103; A61N 5/1031; A61N 2005/1034;
(Continued)

(56) References Cited

U.S. PATENT DOCUMENTS 5,828,221 A * 10/1998 Habraken ............... A61B 6/102
324/662
5,883,935 A * 3/1999 Habraken ............... A61B 6/102
378/117
(Continued)

FOREIGN PATENT DOCUMENTS

WO    2010120534 A1    10/2010
WO    2015017639 A1    2/2015
(Continued)

OTHER PUBLICATIONS

International Search Report and Written Opinion for PCT/EP2017/083656, dated Mar. 19, 2018.
(Continued)

*Primary Examiner* — Allen C. Ho (57) ABSTRACT

A tool for radiation therapy simulation or planning is disclosed which aids in avoiding collisions during treatment. Configurations of components including at least a radiation delivery device (30) and a patient (32) are generated. Each configuration defines positions of the components in a common coordinate system. For each configuration, proximities of pairs of components of the configuration are computed using ray tracing between three-dimensional surface models (30m, 32m, 36m, 38m) representing the components of the pair. A collision is identified as any pair of components having a computed proximity that is less than a margin for the pair of components. Each identified collision is displayed on a display (12), e.g. as a rendering. The simulations or planning may be used to verify deliverability (Continued)

of arc, 4Pi, or static therapy, to determine safety margins for collisions, to calculate and display realizable trajectories, and so forth.

19 Claims, 5 Drawing Sheets

(52) U.S. Cl.
CPC ......... *A61N 5/1036* (2013.01); *A61N 5/1039* (2013.01); *A61N 5/1045* (2013.01); *A61N 5/1047* (2013.01); *A61N 5/1048* (2013.01); *A61N 5/1049* (2013.01); *A61N 5/1077* (2013.01); *A61N 5/1081* (2013.01); *A61N 2005/1034* (2013.01); *A61N 2005/1041* (2013.01); *G16H 20/40* (2018.01)

(58) Field of Classification Search
CPC ................ A61N 5/1036; A61N 5/1039; A61N 2005/1041; A61N 5/1045; A61N 5/1047; A61N 5/1048; A61N 5/1049; A61N 5/1077; A61N 5/1081
USPC ............................................ 378/65, 196–198
See application file for complete search history.

(56) References Cited

U.S. PATENT DOCUMENTS

| | | | | |
|---|---|---|---|---|
| 5,928,149 | A * | 7/1999 | Habraken | A61B 6/102 128/897 |
| 6,408,051 | B2 * | 6/2002 | Habraken | A61B 6/102 324/690 |
| 6,937,951 | B2 * | 8/2005 | Gibb | H03K 17/955 324/674 |
| 7,046,765 | B2 * | 5/2006 | Wong | A61N 5/10 378/117 |
| 7,103,145 | B2 | 9/2006 | Wong | |
| 7,280,633 | B2 | 10/2007 | Cheng | |
| 7,379,533 | B2 * | 5/2008 | Koertge | A61B 6/102 378/117 |
| 7,505,559 | B2 * | 3/2009 | Kuduvalli | A61N 5/1049 378/205 |
| 7,564,949 | B2 * | 7/2009 | Sattler | A61B 6/102 378/117 |
| 7,672,705 | B2 * | 3/2010 | Lachaine | G06T 7/38 600/407 |
| 7,695,192 | B2 * | 4/2010 | Henderson | A61B 6/4458 378/198 |
| 7,835,494 | B2 * | 11/2010 | Nord | A61N 5/1031 378/65 |
| 7,855,656 | B2 * | 12/2010 | Maschke | A61B 6/547 340/686.1 |
| 8,126,114 | B2 * | 2/2012 | Naylor | A61B 34/71 378/65 |
| 8,175,892 | B2 * | 5/2012 | Kapoor | G06Q 10/0633 705/2 |
| 8,416,917 | B2 * | 4/2013 | Maltz | A61N 5/10 378/65 |
| 8,488,741 | B2 * | 7/2013 | Ein-Gal | A61N 5/103 378/117 |
| 8,548,629 | B2 * | 10/2013 | Ortmaier | A61B 6/102 700/255 |
| 8,730,314 | B2 * | 5/2014 | Hannibal | A61B 6/04 348/77 |
| 8,740,880 | B2 * | 6/2014 | Pinault | A61N 5/1049 606/1 |
| 8,855,812 | B2 * | 10/2014 | Kapoor | B25J 9/1666 700/245 |
| 9,301,726 | B2 * | 4/2016 | Mackie | A61B 6/4429 |
| 9,486,647 | B2 * | 11/2016 | Bergfjord | A61N 5/1067 |
| 9,557,158 | B2 * | 1/2017 | Hofmann | A61N 5/1049 |
| 9,750,955 | B2 * | 9/2017 | McNutt | A61N 5/1071 |
| 9,886,534 | B2 * | 2/2018 | Wan | G06F 30/20 |
| 10,201,717 | B2 * | 2/2019 | Berlinger | A61N 5/1049 |
| 10,272,265 | B2 * | 4/2019 | Filiberti | A61N 5/1048 |
| 10,493,298 | B2 * | 12/2019 | Hampton | A61N 5/1049 |
| 10,549,116 | B2 * | 2/2020 | Sheng | A61N 5/1082 |
| 10,660,583 | B2 * | 5/2020 | Haider | A61N 5/1049 |
| 10,692,240 | B2 * | 6/2020 | Mostafavi | G06T 7/74 |
| 11,331,515 | B2 * | 5/2022 | Ranganathan | A61N 5/103 |
| 2011/0054688 | A1 | 3/2011 | Ortmaier | |
| 2011/0224904 | A1 | 9/2011 | Feiten | |
| 2013/0178980 | A1 | 7/2013 | Chemouny | |
| 2015/0035942 | A1 | 2/2015 | Hampton | |
| 2016/0151644 | A1 | 6/2016 | Cheng | |
| 2016/0166856 | A1 | 6/2016 | Popple | |
| 2017/0281975 | A1 | 10/2017 | Filiberti | |

FOREIGN PATENT DOCUMENTS

| | | |
|---|---|---|
| WO | 2016140955 A1 | 9/2016 |
| WO | 2017136551 A1 | 8/2017 |

OTHER PUBLICATIONS

Weller, R. "A Brief Overview of Collision Detection" New Geometric Data Structures for Ollision Detection and Haptics, Jul. 25, 2013.

Chao, Max M. et al "Image display for collision avoidance of radiation therapy: Treatment Planning" Journal of Digital Imaging, vol. 14, No. 4, 2001.

Padilla, Laura et al "Collision predication software for radiotherapy treatments", Medical Physics, vol. 42, No. 11, Nov. 2015.

Becker, Stewart J. "Collision Indicator Charts for Gantry-Couch Position Combinations for Varian Linacs", Journal of Applied Clinical Medical Physics, vol. 12, No. 3, 2011.

Becker, Stewart J. "Collision Indicator Charts for Gantry-Couch Position Combinations for Siemens ONCOR and Elekta Infinity Linacs", Journal of Applied Clinical Medical Physics, vol. 14, No. 5, 2013.

* cited by examiner

FIG. 5

RAY TRACING FOR A DETECTION AND AVOIDANCE OF COLLISIONS BETWEEN RADIOTHERAPY DEVICES AND PATIENT

CROSS-REFERENCE TO PRIOR APPLICATIONS

This application is the U.S. National Phase application under 35 U.S.C. § 371 of International Application No. PCT/EP2017/083656, filed on Dec. 19, 2017, which claims the benefit of U.S. Provisional Patent Application No. 62/438,504, filed on Dec. 23, 2016. These applications are hereby incorporated by reference herein.

FIELD

The following relates generally to the radiation therapy arts, radiation therapy planning arts, and related arts.

BACKGROUND

In radiation therapy, a patient is disposed on a table or other patient support in a treatment delivery room which also contains a linear accelerator (linac) or other radiation therapy beam delivery device (e.g., for delivering a therapeutic x-ray, electron, or proton beam). The radiation delivery device is mounted on a gantry so as to be revolved around the patient. While embodiments in which the radiation delivery device moves respective to a stationary patient are most common and are described here as examples, in some variant designs the radiation delivery device is stationary and a robotic couch moves the patient. In a conventional "step-and-shoot" therapy delivery, the delivery device is rotated using the device gantry between angular therapy delivery positions, with radiation being applied at each delivery position. In continuous delivery modes such as Volumetric Arc Therapy (VMAT), the radiation beam is applied during continuous rotation of the delivery device via the gantry through a delivery arc. In 4 pi delivery modes, the radiation delivery device rotates via its gantry and the patient support is also moved, so as to provide still more freedom to fine-tune the radiation delivery profile. In any such design, the patient may be positioned on the table (or other patient support, such as seated in a chair) with various supporting devices such as knee boards, breast boards, vacuum sealed bags, or so forth. Additionally other devices may be located in the treatment room such as intravascular (IV) fluid delivery support poles, cameras, machine attachments such as cone-beam computed tomography (CT) imaging devices or flat-panel imagers, or the like for monitoring patient position during the therapy delivery, or performing other functions.

There is potential for collision between components in this complex arrangement of moving components. Such collisions may occur during setup, pre-treatment imaging, at therapy positions or as components transition between therapy positions. In addition to actual collisions, it may be desirable to maintain safety or comfort margins between components. For example, the patient may be uncomfortable or become claustrophobic if the radiation delivery device comes too close to the patient.

The following discloses a new and improved systems and methods that address the above referenced issues, and others.

SUMMARY

In one disclosed aspect, a radiation therapy simulation or planning device is disclosed, including a computer, a display, and a non-transitory storage medium. Said medium stores instructions readable and executable by the computer to perform operations including: generating configurations of components including at least a radiation delivery device and a patient wherein each generated configuration of components defines positions of the components in a common coordinate system; for each configuration, computing proximities of pairs of components of the configuration and identifying a collision as any pair of components having a computed proximity that is less than a margin for the pair of components; and displaying on the display each identified collision.

In another disclosed aspect, a radiation therapy simulation or planning device is disclosed, including a computer and a non-transitory storage medium storing instructions readable and executable by the computer to perform operations including: generating configurations of components including at least a radiation delivery device and a patient wherein each configuration of components defines positions of the components in a common coordinate system; for each configuration, computing proximities of pairs of components of the configuration using ray tracing and identifying a collision as any pair of components having a computed proximity that is less than a margin for the pair of components; and updating the generated configurations to eliminate any identified collision.

In another disclosed aspect, a radiation therapy device includes a radiation therapy planning device as set forth in the immediately preceding paragraph and a radiation delivery device. The radiation delivery device is operative to deliver stepwise radiation therapy to the patient in accordance with the generated radiation therapy delivery plan. In continuous arc delivery embodiments, the radiation delivery device applies therapeutic radiation to the patient during traversal of an arc between successive control points of the sequence of control points. In stepwise delivery embodiments, the radiation delivery device applies therapeutic radiation to the patient at successive control points of the sequence of control points and does not apply therapeutic radiation to the patient during traversal between successive control points of the sequence of control points.

In another disclosed aspect, a radiation therapy planning method is disclosed. A radiation therapy delivery plan is generated using a computer. The plan comprises radiation delivery settings at a plurality of control points, and the radiation delivery settings are optimized respective to a set of dose objectives. Each control point is defined by a configuration of components including at least a radiation delivery device and a patient. The configuration of components defines positions of the components in a common coordinate system. For the configuration of each control point of the radiation therapy delivery plan and for each of a plurality of configurations between the control points traversed during execution of the radiation therapy delivery plan, proximities of pairs of components of the configuration are computed using three-dimensional surface models representing the components of the pair, and a collision is identified as any pair of components having a computed proximity that is less than a margin for the pair of components. The computing of the proximity and the identifying are performed by the computer. Each identified collision is displayed on a display.

One advantage resides in detecting potential collisions during the radiation therapy planning stage and optionally prior to the dose optimization computation.

Another advantage resides in providing early detection of unsafe or uncomfortably close approaches between components prior to the planning of the radiation therapy session.

Another advantage resides in providing automated adjustment of the sequence of control points (CPs) for use in generating an intensity modulated radiation therapy (IMRT) plan in order to avoid collisions or unacceptably close approaches between components.

Another advantage resides in providing visualization of the spatial arrangement of components during radiation therapy planning or earlier, e.g. after the patient computed tomography (CT) scanning is performed but prior to dose optimization. Earlier detection of collisions, e.g. in simulation, can for example allow the therapist to adjust the desired isocenter position (marking locations) for use in planning and delivery later on.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
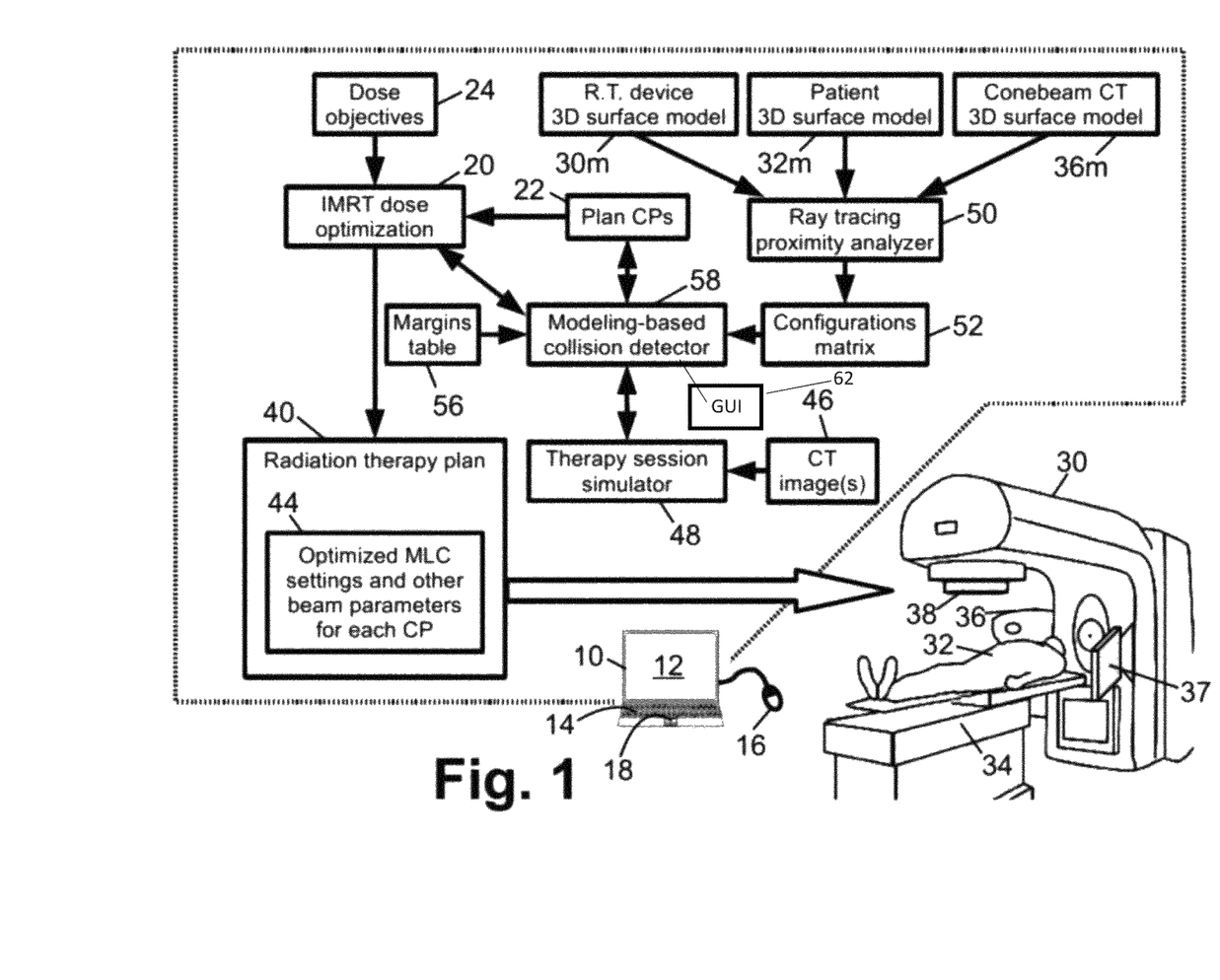
FIG. 1 diagrammatically shows an illustrative system for performing collision detection during therapy simulation to adjust the patient's position and/or the position of other components in the therapy room to avoid collisions that may occur during delivery prior to the radiation therapy planning. Also shown is the generation of a sequence of control points (CPs) during radiation therapy planning. This may be any radiation therapy plan employing a sequence of CPs that can benefit from the execution of the collision detection algorithm either post plan creation or as input to the CP generation.

With reference to FIG. 1, an radiation therapy planning system that provides collision detection is described. The planning is executed by an electronic processor, e.g. an illustrative computer 10, which reads and executes instructions stored on a non-transitory storage medium (not shown). The electronic processor 10 may, for example, be embodied as the illustrative computer 10 (e.g. a desktop computer, network-based server computer, computer cluster, cloud computing resource including an ad hoc combination of computers that may change over time, various combinations thereof, or so forth) that executes instructions read from one or more non-transitory electronic storage media (e.g. one or more hard drives, optical disks, solid state drives or other electronic digital storage devices, various combinations thereof, or so forth) that stores the instructions. The computer 10 includes or has operative access to at least one display 12 (e.g. an LCD display, plasma display, or so forth) and one or more user input devices (e.g. an illustrative keyboard 14, mouse 16, trackpad 18, touch-sensitive overlay of the display 12, and/or so forth).

The electronic processor 10 may be programmed to perform IMRT (or other) dose optimization 20 for a sequence of control points (CPs) 22 to achieve a set of radiation dose objectives 24 usually expressed as an average or minimum dose to be delivered to a target region (e.g. a malignant tumor) and dose limits for one or more organs at risk (OARs). Manual generation of the CPs 22 may also be done by the planner. As is known in the art, the IMRT optimization typically receives as inputs the set of radiation dose objectives 24 and anatomical information, e.g. in the form of a intensity map of the patient generated from a planning image acquired by computed tomography (CT) imaging, magnetic resonance (MR) imaging, or the like. The planning image is typically segmented to identify regions of different tissues or organs; such segmentation may be manual (e.g., the oncologist defines the regions by drawing contours in the planning image), automated (e.g. using edge detection or other appropriate image processing), or semi-automated. Each CP 22 is defined by a configuration of components present in the radiation therapy laboratory during the radiation therapy session. These components include at least a radiation delivery device 30 and a patient 32 (disposed on a patient support 34), and may include other devices such as a conebeam computed tomography (CT) imager (including an x-ray source 36 and x-ray detector panel 37) that may be employed in the radiation delivery room to monitor the patient 32. The illustrative radiation delivery device 30 is a linear accelerator (linac) having a radiation delivery head or emission orifice 38 that outputs a therapeutic radiation beam (which may be an electron beam, x-ray beam, or so forth depending on the type of radiation therapy). For example, the illustrative radiation delivery device 30 could be a TrueBeam™ radiotherapy system (available from Varian Medical Systems), which includes four components that introduce salients: the radiation delivery head/arm assembly; side-positioned x-ray source and detector array components for an integrated conebeam computed tomography (CT) imager; and an accessory module (no analog shown in FIG. 1) positioned across the patient from the delivery head/arm assembly. Each of these salients present a potential collision point that must be considered during setup of the sequence of control points for use in the radiation therapy delivery. The radiation delivery device 30 may take other forms, e.g. a cyclotron and associated beam forming/shaping nozzle configured to generate a therapeutic proton or neutron beam.

The configuration defines the positions of the components at the control points (CPs) 22 in a common coordinate system. In standard radiation therapy the configuration may vary among successive control points (CPs) 22 due to rotation of the radiation delivery device 30 around the patient 32. In 4 Pi radiation therapy both the radiation delivery device 30 and the patient support 34 may move to provide a wider range of achievable configurations.

The IMRT dose optimization 20 typically operates by optimizing radiation delivery settings such as beam-on time, multi-leaf collimator (MLC) settings for shaping the beam, and so forth at each control point so that the cumulative dose delivered to the target region and any OARs satisfies the set of radiation dose objectives 24. In a stepwise radiation therapy session the radiation is delivered only at the control points, with the radiation delivery head 38 held stationary at each control point (CP) 22. In continuous arc delivery approaches such as Volumetric Arc Therapy (VMAT), the radiation beam is applied during continuous rotation of the radiation delivery device 30 via its gantry through a delivery arc, and the number of control points (CPs) 22 is chosen to be high enough so that the radiation delivery settings can be interpolated between control points (CP) 22 to control delivery continuously over the continuous arc. It is also noted that while the single delivery head 38 is illustrated, in other embodiments there may be two or more delivery heads in order to simultaneously irradiate the patient 32 from two or more directions. The IMRT dose optimization 20 can employ any suitable optimization routine, and in some embodiments employs commercially available IMRT optimization products such as the Pinnacle$^3$ Treatment Planning tool available from Koninklijke Philips N. V., Eindhoven, Netherlands. In some embodiments, the IMRT dose optimization 20 may adjust the control points (CPs) 22 to better achieve the set of radiation dose objectives 24; in other embodiments the control points (CPs) 22 are fixed during the IMRT dose optimization 20. It should also be noted that the term "optimization" and similar phraseology does not necessarily connote that the absolute best solution is achieved; rather, the optimization is sufficient to achieve the set of radiation dose objectives 24 within specified tolerances.

The output of the radiation therapy plan 40 comprising radiation delivery settings 44 at the sequence of plan control points (CPs) 22. Each control point (CP) 22 is defined by a configuration of the components 30, 32, 36. At a minimum, the components of the configuration include at least the radiation delivery device 30 and the patient 32. The configuration of components defines the positions of the components in a common coordinate system. In addition to the control points (CPs} 22, a plurality of configurations between control points of the sequence of control points (CPs) 22 are traversed during execution of the radiation therapy delivery plan, e.g. during rotation of a gantry of the radiation delivery device 30 from one control point (CP) 22 to the next, and (in techniques such as 4 pi radiation delivery) possible concomitant movement of the patient 32. The radiation therapy plan 40 is suitably executed by the radiation delivery device 30 applying radiation to the patient 32 using the beam-on time, MLC settings, trajectories defined by the CPs 22, and other parameters of the radiation therapy plan 40. The radiation therapy plan 40 may employ a 4 pi delivery mode, stepwise delivery with radiation being delivered only at the successive CPs 22, or a continuous arc therapy mode such as Volumetric Arc Therapy (VMAT).

Usually, prior to a generation of the radiation therapy plan 40 (and, of course, therefore prior to actual delivery of the radiation therapy), a simulation stage is done for most cancer patients in which they are imaged usually with computed tomography (CT) imaging, although magnetic resonance (MR) scanning may be used for the planning imaging. The CT (or MR) imaging to produce one or more CT (or MR) planning images 46, and a simulator 48 simulates the intended radiation therapy session to define the geometry, identify areas of the body to be exposed to ionizing radiation and areas to be blocked or shielded from radiation, prior to dose optimization and the actual treatment. The simulator 48 provides information on the patient's anatomy in the treatment position and localizes the patient's position during treatment. In some embodiments disclosed herein, this simulation stage incorporates collision detection as disclosed herein, run with a simulated in-room delivery at the time of simulation, to give the simulation therapist a sense of whether the patient's physical setup will be usable at the time the delivery happens or when the radiation therapy plan is performed. In this approach, the collision detection disclosed herein is used well before the planning stage (or control points) are executed. The therapist can thereby use feedback from the simulation to adjust the patient's position to mitigate any potential collisions later on.

With continuing reference to FIG. 1, the sequence of control points (CPs) 22 is calculated prior to performing the radiation therapy plan to detect and avoid collisions. The IMRT optimizer (if utilized in the planning process) may take this as input in determining its optimized plan. Planning of the trajectory passing through the control points (CPs) 22 may be performed after the IMRT optimization, or during the optimization. The collision detection is performed for potential trajectories in developing the plan control points (CPs) 22 and configurations between control points that are to be traversed during execution of the ultimately developed radiation therapy delivery plan. The illustrative collision detection employs three-dimensional (3D) surface models to model or simulate the components that will be present in the radiation therapy delivery room during the radiation therapy session, and that could be involved in a collision. For the illustrative example, the components include the radiation therapy delivery device 30, the patient 32 (broadly construed as a component for the purposes of collision detection), and the monitor device, i.e. the conebeam CT 36, 37. Corresponding to these physical components are representative 3D models, namely a radiation therapy (R.T.) device 3D surface model 30m, a patient 3D surface model 32m, and a monitor device 3D surface model 36m. The 3D surface models 30m, 32m, 36m of the respective physical components 30, 32, 36 may be generated in various ways. In the following, some illustrative examples of ways of generating these surface models are set forth—it is to be understood that these are non-limiting illustrative examples and that the various 3D surface models may be generated in other ways. In some illustrative non-limiting examples, for standardized commercial components such as the radiation therapy delivery device 30 and possibly the monitor device 36, the corresponding 3D surface model 30m, 36m may be generated by the manufacturer using 3D scanning, e.g. using a coordinate measuring machine (CMM), or LADAR, or so forth. As another non-limiting illustrative example, in the case of the patient 32 the corresponding patient 3D surface model 32 may be generated, for example, using an in-house 3D scanner, or a range camera, or any means to generate VTK mesh models of a generic human body surface or physical devices used in the room (e.g. pillows, knee supports, et cetera). Likewise, the radiation therapy device 3D model 30m can combine a 3D scanned model or inputted dimensions e.g. CAD drawing of the linac and a 3D scanned model of a collimator add-on to generate the radiation delivery head 3D model portion 38m of the radiation therapy device 3D model 30m. These models, however generated, may be combined with the imaged patient e.g. via CT, to aid in creating a 3D representation of the therapy delivery room.

However the surface models 30m, 32m, 36m of the respective physical components 30, 32, 36 are generated, these models are imported or input to the ray tracing system. Optionally, surface portions of the modeled components 30, 32, 36 which may not be included in the imported surface models may be generated by estimated extensions, e.g. of arms/legs/devices that are not in the CT or other scan employed in generating the imported model. A graphical user interface (GUI), computer aided design (CAD) drawing, or other available information may additionally or alternatively be leveraged in generating (or extending) the surface models 30m, 32m, 36m. The component modeling is also preferably extensible in order to add surface models for representing patient fixation devices or other patient-specific devices as models and allow users to drag and drop them into the configuration.

For a given configuration (which could be a CP, or could be a configuration along a possible trajectory being simulated during the initial simulation phase 48), the various components 30, 32, 36 are represented by their respective 3D models 30m, 32m, 36m positioned in a common coordinate system. (Note that FIG. 1 includes illustrative components, but numerous other components which may be moving are contemplated to be similarly modeled, e.g. patient fixation devices). A typical choice of common coordinate system used in radiation therapy planning is the world coordinate system, which is centered on the isocenter of the radiation therapy device 30; however, another common coordinate system may be chosen for use in the collision detection computations. With the 3D models 30m, 32m, 36m positioned in the common coordinate system, a ray tracing proximity analyzer 50 computes a proximity of each pair of components of the configuration. The ray tracing employs parallel rays (or, in other embodiments, non-parallel rays) extending between the three-dimensional surface models of each pair of components of the configuration, and the proximity between the pair of components corresponds to the shortest ray. This is repeated for each pair of components of the configuration. In general, if there are n components then the number of pairs that need to be computed is given by the binomial coefficient $$\binom{n}{2} = \frac{n(n-1)}{2},$$

e.g. three pairs in the case of three components, six pairs in the case of four components, ten pairs in the case of five objects, and so on.

The foregoing ray tracing proximity analysis performed for each configuration generates a configurations matrix 52 storing, for each processed configuration, the proximity between each pair of components as a function of time, CP, or other metric. In some embodiments, the configurations matrix 52 includes only the configurations of the plan CPs 22 of the radiation therapy delivery plan 40 and the configurations traversed in moving between those CPs 22. In other embodiments, the ray tracing proximity analyzer 50 is applied to compute the proximity of each pair of components for all credible configurations that could be employed that is to say, for all possible (credible) combinations, so that they are available for the initial simulation phase as the simulation therapist explores possible delivery trajectory options using the therapy session simulator 48. In this case, all the processed configurations can also later be fed to the radiation therapy planning device 20 for use in trajectory tuning or optimization including identifying any collisions at the particular CPs of the sequence of plan CPs 22 and the intervening configurations traversed when moving between CPs. In either approach, the configurations are preferably computed for a chosen resolution of movement when traversing between configurations. For example, the resolution may employ (as a non-limiting example) five degree rotation increments of the radiation delivery gantry and three degree rotational increments for the patient support 34.

To perform collision detection, the configurations matrix 52 is input to a modeling-based collision detector 58 which models the configurations using the 3D models 30m, 32m, 36m and detects whether any of the proximity values indicate a collision. While strictly speaking a "collision" would ordinarily imply the two components making up the pair of components actually contact each other (so that the shortest ray would be zero or negative), in practice it is generally preferable to define a margin (e.g. stored in a margins table 56) for each pair of components, and to define a collision as the proximity (shortest ray) being less than the chosen margin for the pair of components. The margins 56 may be chosen to ensure safety by making the margin for a pair of components larger than the statistical uncertainty in position of the components. In some cases, the margin may be chosen to be larger than this. For example, although the statistical uncertainty of the radiation delivery head 38 may be small, the margin for the pair consisting of the radiation delivery head 38 and the patient 32 may be chosen to be larger than the statistical uncertainty due to the likelihood that a close pass of the delivery head 38 to the patient's body will be discomforting for the patient. Thus, in general, a collision is identified in a configuration as any pair of components whose proximity (shortest ray in the ray tracing) is less than the margin (e.g. stored in the margins table 56) for the pair of components.

Thus, in one illustrative embodiment, therapy session simulator 48 is invoked by the simulation therapist, treatment planner, or other medical professional, which allows for exploration of various possible therapy delivery implementations. If an explored implementation would traverse a configuration indicated by the modeling-based collision detector 58 as having a collision, then an editor or other graphical user interface 62 of the modeling-based collision detector 58 illustrates the collision using a 3D rendering of the 3D surface models 30m, 32m, 36m positioned in the common coordinate system in accordance with the configuration containing the collision. The user may then choose to adjust the explored trajectory (or the control point if a sequence of control points for a specific therapy plan is being set up) in order to eliminate the collision. Once the user settles on the geometry and exposure regions for the radiation therapy, the sequence of plan CPs 22 is calculated and/or optimized 20 into a set of control points.

In some embodiments, during the IMRT dose optimization 20 the plan CPs 22 are treated as plan parameters which are optimized along with other plan parameters (MLC settings, et cetera), and if a thereby adjusted CP is indicated as having a collision, the CP containing the collision is adjusted automatically, without user intervention.

In a variant embodiment, the configuration matrix 52 does not include any configurations having collisions, and so the IMRT dose optimization 20 cannot select any sequence of CP with collisions.

Figure 2:
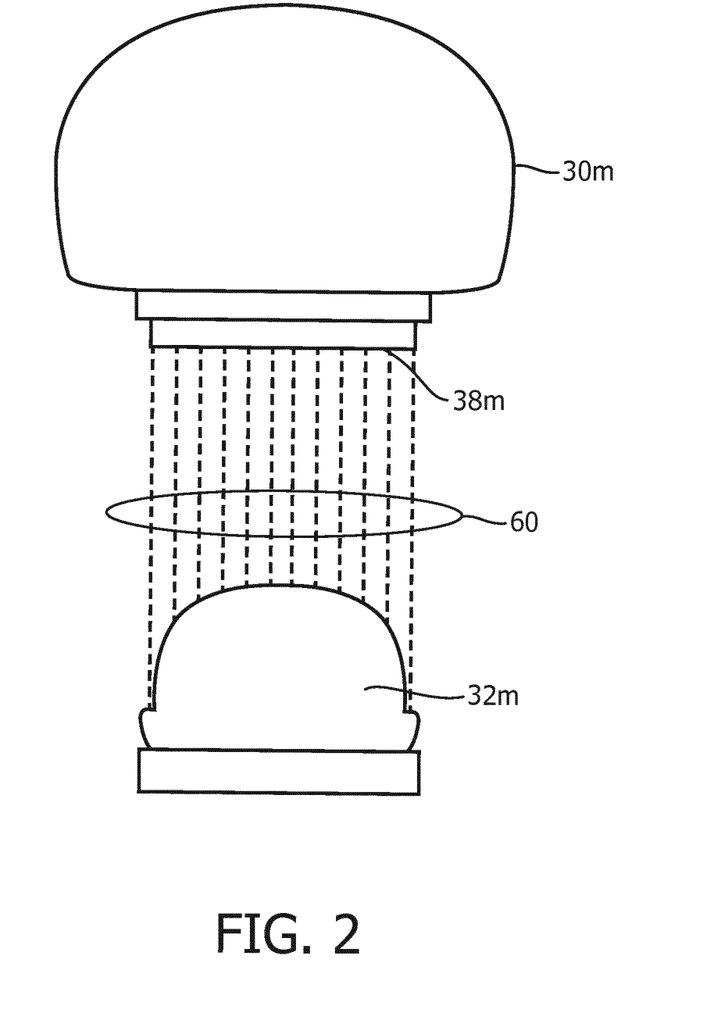
FIG. 2 diagrammatically shows ray tracing for collision detection performed by the ray tracing proximity analyzer of FIG. 1.
Figure 3:
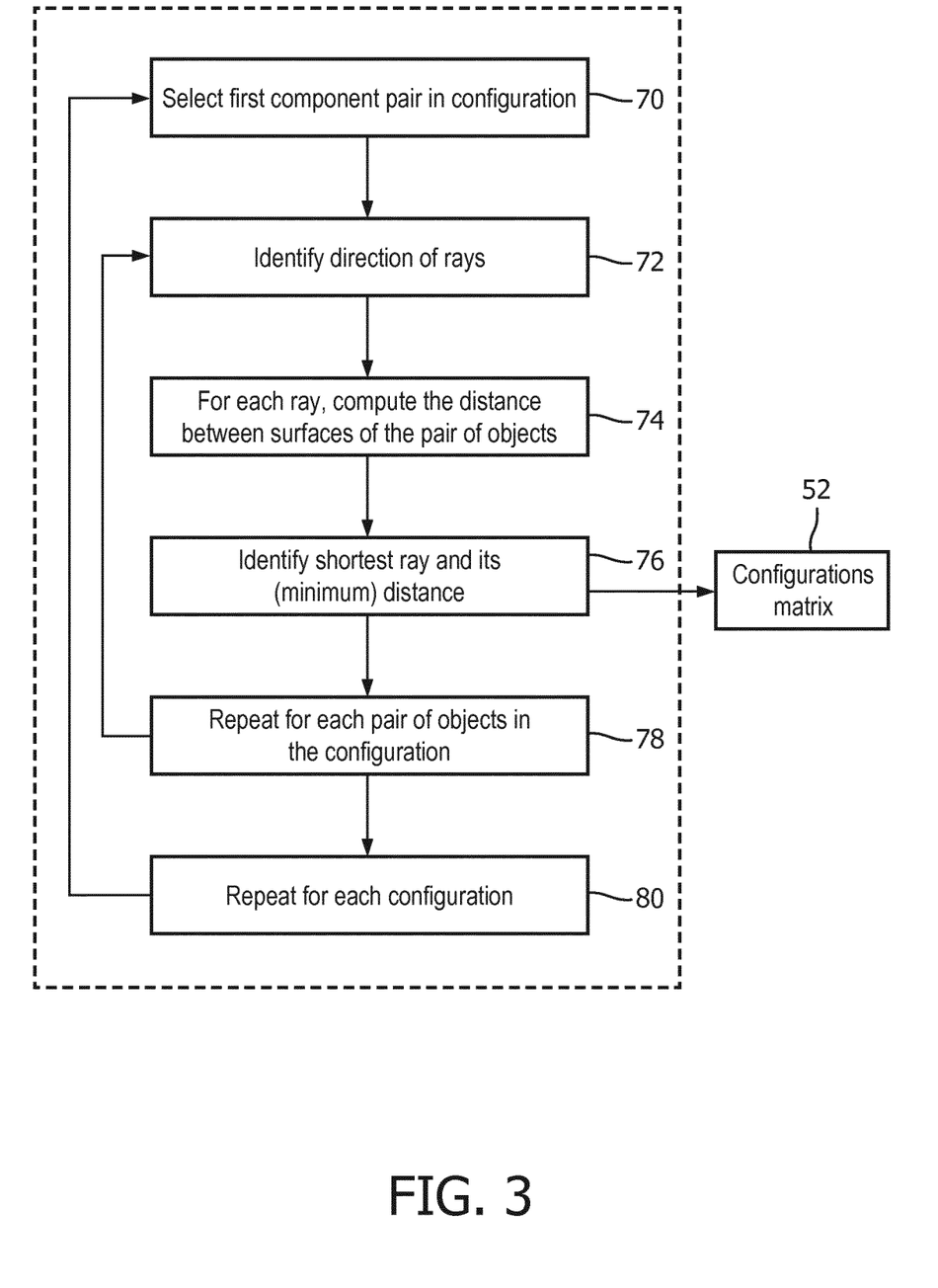
FIG. 3 diagrammatically shows processing performed by the ray tracing proximity analyzer of FIG. 1.

With continuing reference to FIG. 1 and with further reference to FIGS. 2 and 3, an illustrative example of processing performed by the ray tracing proximity analyzer 50 is described. FIG. 2 shows the ray tracing processing for assessing proximity between the patient 32 and the radiation delivery head 38 of the radiation delivery device 30. The ray tracing proximity determination includes computing the lengths of mutually parallel rays 60 extending between the pair of component 3D surface models including the radiation therapy device 3D model 30 (and more precisely the radiation delivery head 3D model 38*m*) and the patient 3D model 32*m*. While a single slice is depicted in FIG. 2, it will be appreciated that the ray tracing is likewise performed for multiple parallel planes, and the shortest ray is chosen as the proximity of the two components 32, 38 of the respective pair. This proximity calculation is repeated for each pair of components that are susceptible to collision, e.g. between the radiation delivery device 30 and the x-ray tube 36, between the radiation delivery device 30 and the x-ray detector panel 37, between the x-ray tube 36 and the patient 32, between the x-ray detector panel 37 and the patient 32, or so forth. Some pairs of components may not be physically capable of colliding (for example, the integrated x-ray tube 36 and detector panel 37 may be mounted on the gantry of the radiation delivery device 30 such that the two components 36, 37 can never collide) in which case no proximity calculation is performed for those pairs. The processing flow performed by the ray tracing proximity analyzer 50 is diagrammatically shown in FIG. 3. In an operation 70, a first component pair in a configuration is selected (e.g. the components 30, 32). In an operation 34, the direction of the mutually parallel rays is selected. This may, for example, entail selecting a centroid of each component 3D model and defining the direct as the direction of the line connecting the two centroids. In an operation 74, the rays between the 3D component models in the configuration are constructed (e.g. rays 60 between component 3D surface models 30*m*, 32*m* in illustrative FIG. 2) and the lengths of the rays determined (e.g. the intersection of the ray with the surfaces of the two 3D surface models are identified and the Euclidean distance between the two intersection points computed). In an operation 76, the shortest such ray is identified as the proximity of the two components 30, 32 (that is, as the minimum distance between the two components 30, 32 in the configuration). In a loop 78, the operations 72, 74, 76 are repeated for each component pair of the configuration that is susceptible to collision (e.g. for the component pair 32, 36 and for the component pair 30, 36 in the example of FIG. 2) so as to identify the proximity of each pair of objects in the configuration. In a loop 80, the operations 70, 72, 74, 76, 78 are repeated for each configuration for which proximities are to be computed. The resulting data, i.e. the proximity of each pair of components in each processed configuration, is stored in the configurations table 52.

Figure 4:
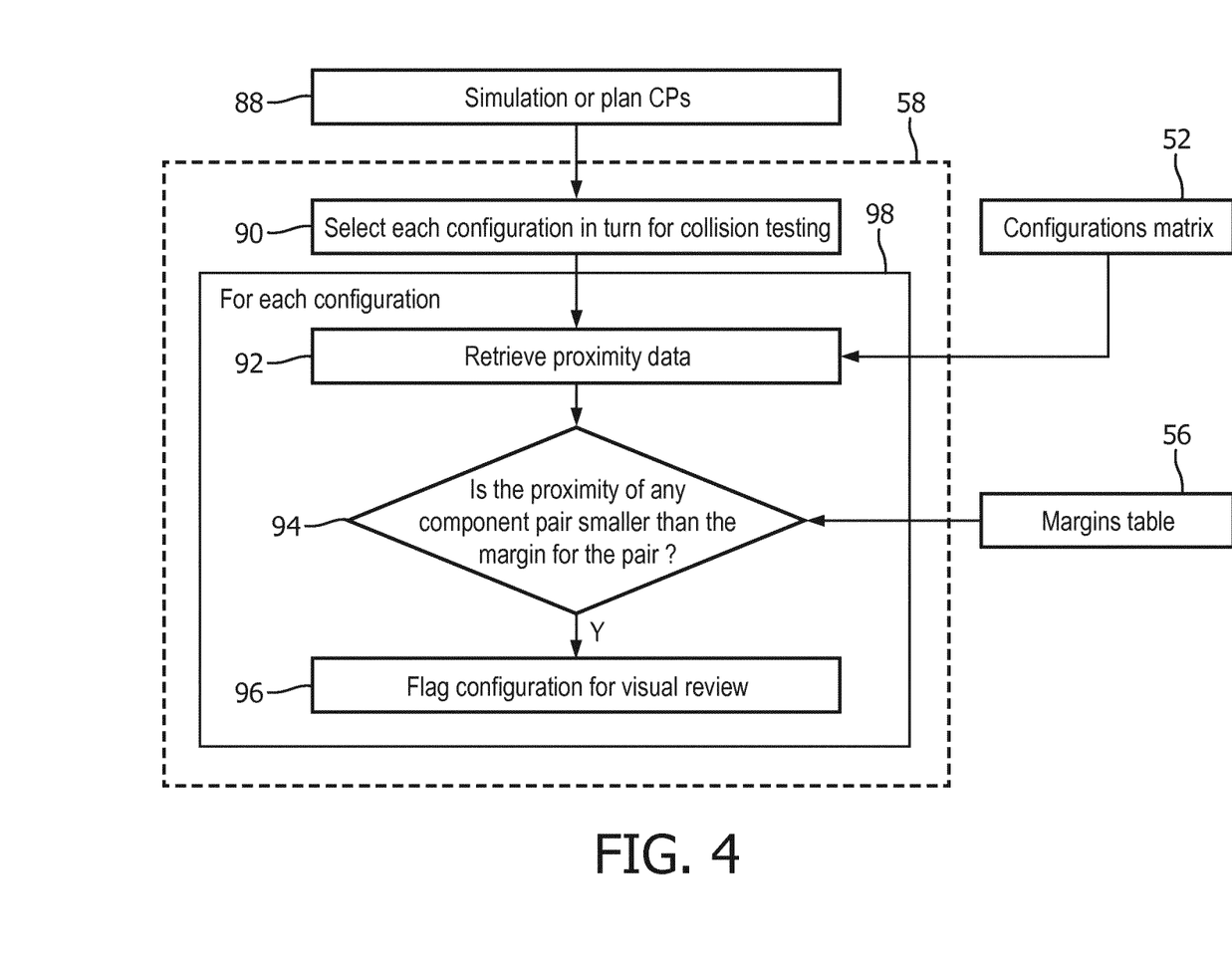
FIG. 4 diagrammatically shows collision detection performed by the modeling-based collision detector of FIG. 1 using ray tracing as described in FIG. 2 and FIG. 3.

With reference to FIG. 4, an illustrative embodiment of the collision detection performed by the modeling-based collision detector 58 of FIG. 1 is diagrammatically shown. A set of configurations 88 to be checked for collisions is input, e.g. to the therapy session simulator 48 used by a simulation therapist in the simulation stage, or the plan CPs 22 during the later radiation therapy plan. In this illustrative example, it is assumed that the configurations table 52 contains proximity data for all credible configurations. In an operation 90, each configuration is selected in turn for collision testing. The configurations traversed between CPs are suitably determined from the movement of the various components, e.g. the rotation speed of the radiation therapy device gantry, movement speed of the patient support, and so forth. In an operation 92, the proximity data for the configuration is retrieved from the configurations matrix 52. In an operation 94 the proximity of each component pair is compared against the margin (from the margins table 56). If the proximity of any component pair is determined in operation 94 to be smaller than its margin, then in an operation 96 the configuration is flagged (i.e. identified, queued, et cetera) for visual review. In an alternative embodiment of operation 96, the configuration having a collision is removed from the configurations matrix 52 so that it cannot be selected. Again, it is noted that in the decision operation 94 a collision is identified if the proximity is smaller than the margin, and that margin may be greater than zero (although a zero value for a margin is also contemplated). The processing 92, 94, and (if needed) 96 is repeated for each configuration selected in turn in the operation 90 in order to check that all configurations during the pre-planning simulation of a generic, representative, rough plan of CPs or the CP sequence specifically designed during planning.

With reference back to FIG. 1, the modeling-based collision detector 58 is contemplated to be integrated into various radiation therapy planning packages, such as the Pinnacle³ Treatment Planning tool available from Koninklijke Philips N. V., Eindhoven, Netherlands, and/or into CT or MR scanner control/simulation packages used to acquire the planning image and/or used by the simulation therapist in performing the pre-planning simulation phase. For example, the IMRT planning or CT or MR control/simulation package preferably includes or provides user dialogs (not shown) via which a user can create and/or load the 3D surface models 30*m*, 32*m*, 36*m* and via which the user can input the margins between various component pairs so as to populate the margins table 56 (there may optionally be default margin values). The modeling-based collision detector 58 also communicates identified collisions to the user, and to receive edits to the simulated therapy or planned CPs to avoid such collisions.

To illustrate a collision, the 3D component models 30*m*, 32*m*, 36*m* are suitably rendered on the display 12 in their positions in the common coordinate system for the configuration containing the collision. Optionally, the collision point is highlighted or flagged on the display. Optionally, the user may select to move one or both of the colliding components by clicking on and moving the corresponding 3D surface model so as to adjust the configuration to avoid the collision. After adjusting the configuration, the collision detection may be repeated to determine whether the adjustment was sufficient to eliminate the collision. In an alternative remedial action, the user might elect to decrease the margin for the two colliding components to a smaller value so as to permit the simulated proximity. In other embodiments, it is contemplated to employ a less detailed output for displaying identified collisions. For example, the display 12 could list the configurations containing identified collisions and the pair of components in each such configuration that are identified as colliding, without providing a 3D rendering of the identified collisions.

Figure 5:
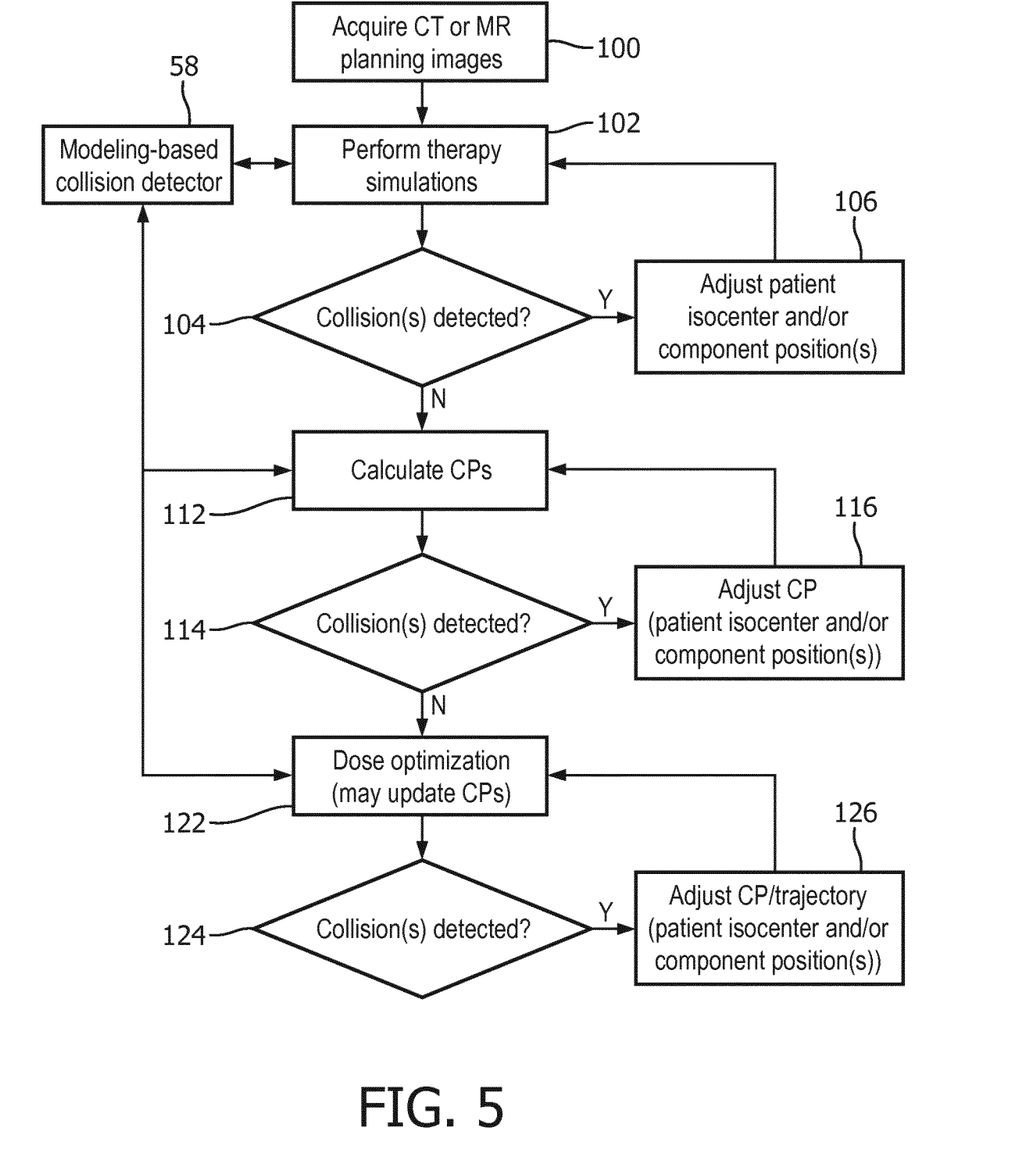
FIG. 5 diagrammatically shows a radiation therapy diagnosis, therapy simulation, and dose optimization workflow illustrating various points at which the disclosed modeling-based collision detector may be advantageously employed to provide early detection and resolution of possible patient-component and/or component-component collisions.

With reference to FIG. 5, the modeling-based collision detector 58 of FIG. 1 may be integrated into the radiation therapy simulator 48 and/or planning package 20 to provide collision detection at various phase(s) in the diagnosis, therapy simulation, and therapy planning phases of the treatment. As diagrammatically shown in FIG. 5, in a typical workflow, upon diagnosis and determination by an oncologist or other medical professional that radiation therapy is indicated, the patient is scheduled for a CT or MR imaging session to acquire CT or MR planning images 100. These are initially used to perform therapy simulations 102 using the therapy session simulator 48 to define and identify of the areas of the body to be exposed to ionizing radiation prior to the actual treatment. The simulations also identify areas to be blocked or shielded from radiation. The modeling-based collision detector 58 may be invoked during these simulations, using the retrieved models 30*m*, 32*m*, 36*m* and/or a patient specific or non-specific radiation therapy plan from a database, to detect possible collisions. If one or more such collisions are detected as indicated in operation 104, the modeling-based collision detector 58 displays a 3D rendering of the collision using 3D renderings of the models 30m, 32m, 36m, and the user may make patient isocenter and/or component position(s) adjustment(s) 106 (or, as mentioned previously, the margins 56 may be adjusted) to remediate the possible collision, after which the simulation 102 may be repeated. This simulation sequence may be repeated in iterative fashion to define a therapy that provides ionizing radiation exposure to the desired areas, while shielding critical areas from radiation expose, and also avoiding collisions using the modeling-based collision detector 58.

With continuing reference to FIG. 5, after the simulation phase the radiation therapy planning is performed. To this end, the control points (CPs) are calculated in an operation 112. These are the CPs 22 along the trajectory for performing the radiation therapy planning 20. Again, the modeling-based collision detector 58 may be invoked to check the chosen CPs for possible collisions, and if collision(s) are detected as indicated in operation 114, the modeling-based collision detector 58 displays a 3D rendering of the collision using 3D renderings of the models 30m, 32m, 36m, and the user may adjust one or more CPs by making patient isocenter and/or component position(s) adjustment(s) 116 (or, as mentioned previously, the margins 56 may be adjusted) to remediate the possible collision, so as to produce updated CPs. Again, this process may be repeated to calculate a set of CPs for the radiation therapy planning.

With continuing reference to FIG. 5, after the CPs are calculated, the dose optimization may be performed in an operation 122 using the dose optimizer 20. This generally entails optimizing MLC settings, beam-on time, and so forth to achieve chosen clinical dose objectives, e.g. maximum and/or average dose to the target (e.g. tumor), maximum permissible dose to organs at risk, or so forth. The dose optimization may in some optimization frameworks include optimizing the CPs and/or the trajectories of components such as the linac radiation delivery head 38 and/or the patient table 34, and such adjustments could lead to possible collisions. Thus, the modeling-based collision detector 58 may be invoked to detect collisions introduced during the dose optimization 122. If collision(s) are detected as indicated in operation 124, then one or more CPs and/or the trajectory connecting the CPs may be adjusted in an operation 126. The adjustment 126 may be manual, e.g. the modeling-based collision detector 58 displays a 3D rendering of the collision using 3D renderings of the models 30m, 32m, 36m, and the user may adjust one or more CPs. Alternatively, an automated adjustment may be performed to avoid the collision as part of the optimization 122. The resulting radiation therapy plan providing the desired dose delivery is then employed in the radiation therapy delivery.

As is known in the art, the radiation therapy may be performed using a fractionated delivery, in which the patient returns for successive radiation therapy sessions over which the full radiation dose is delivered. In such a case, it is contemplated for various portions of the workflow of FIG. 5 may be repeated to simulate and optimize successive fraction sessions, and again the modeling-based collision detector 58 may be employed in these successive simulation/optimization sessions to provide early detection and remediation of collisions.

In the disclosed approach, ray tracing is used in conjunction with realistic 3D surface models of the components in order to identify collisions, in the pre-planning simulation phase 48 and/or during the Radiation Treatment planning 20. This approach advantageously accounts for the detailed surfaces of the components and their spatial relationships. However, other collision detection techniques besides ray tracing may be used, such as by adding dilation to each 3D surface model and detecting a collision as an overlap at the voxel level between two dilated surface models. For example, if the surface of the patient 3D surface model 32 and the conebeam CT surface model 36 are each dilated by 10 cm, then a collision between the camera and the patient is detected as voxel overlap if the CT comes within 20 cm of the patient.

The disclosed collision detection approaches can be used in a variety of ways such as: 1) a quality assurance check to determine if arc, 4Pi, or static therapy is truly deliverable prior to physically attempting the delivery including all available 3D models of in-room devices, 2) to determine allowed beam angle positions prior to creating the treatment plan for/during IMRT or manual planning, 3) to determine and incorporate safety margins for collisions into the treatment plan, 4) to provide a matrix of possible collisions as input into the dose optimization algorithm 20, 5) to calculate and display trajectories such that the desired treatment plan is deliverable between planned CPs, 6) for reduction of patient dose due to scatter off accessories or beam source widening, or so forth, 7) for estimation of potential collisions prior to treatment plan creation during the CT (or MRI or other) simulation so that it can be known during this stage whether the patient needs to be re-imaged (re-simulated, re-situated) in a different position to avoid potential collisions detected during the treatment planning and delivery process, and/or 8) to provide an interface to import and model the 3D representation and position of all desired devices in the treatment room.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:
1. A radiation therapy simulation or planning device comprising:
   a computer;
   one or more user input devices;
   a display; and
   a non-transitory storage medium storing instructions readable and executable by the computer to perform operations including:
      generating configurations of components including at least a radiation delivery device and a patient, wherein each configuration of the generated configurations of components defines positions of the components in a common coordinate system;
      maintaining a margins table storing margins including a margin for each pair of components, wherein the maintaining the margins table includes receiving a user entry or editing of the margins stored in the margins table via the one or more user input devices;
      for each configuration of the generated configurations of components, computing, using ray tracing, proximities of pairs of components of a configuration, and identifying a collision of a pair of components having a computed proximity that is less than a margin for the pair of components; and displaying on the display the identified collision of the pair of components.

2. The radiation therapy simulation or planning device of claim 1, wherein the computing the proximities of the pairs of components of the configuration using ray tracing employs a three-dimensional surface model representing each component of the pair of components, and the ray tracing employs parallel rays extending between three-dimensional surface models of the pair of components of the configuration.

3. The radiation therapy simulation or planning device of claim 2, wherein the displaying on the display the identified collision includes displaying a three-dimensional rendering of the configuration containing the identified collision, the three-dimensional rendering including renderings of the three-dimensional surface models representing the pair of components, and further displaying an indication of the identified collision in the three-dimensional rendering of the configuration containing the identified collision.

4. The radiation therapy simulation or planning device of claim 2, wherein the three-dimensional surface model representing each component of the pair of components comprises a surface model.

5. The radiation therapy simulation or planning device of claim 4, wherein the generating the configurations of components includes:
generating the configurations of components as a sequence of control points of a radiation therapy delivery plan comprising radiation delivery settings at each control point of the sequence of control points.

6. The radiation therapy simulation or planning device of claim 1, wherein the generating the configurations of components includes:
generating the configurations of components for a radiation therapy delivery simulation performed prior to performing radiation therapy delivery planning.

7. The radiation therapy simulation or planning device of claim 1,
wherein the operations further include: providing a modelling-based collision detector and a user interface component of the modeling-based collision detector for user editing of the generated configurations of components.

8. A radiation therapy simulation or planning device comprising:
a computer;
one or more user input devices; and
a non-transitory storage medium storing instructions readable and executable by the computer to perform operations including:
generating configurations of components including at least a radiation delivery device and a patient, wherein each configuration of the generated configurations of components defines positions of the components in a common coordinate system;
providing a modeling-based collision detector and a user interface component of the modeling-based collision detector for user editing of the generated configurations of components;
for each configuration of the generated configurations of components, computing proximities of pairs of components of a configuration using ray tracing, and identifying a collision of a pair of components having a computed proximity that is less than a margin for the pair of components; and
updating the generated configurations of components to eliminate the identified collision of the pair of components.

9. The radiation therapy simulation or planning device of claim 8, wherein the computing the proximities of the pairs of components of the configuration using ray tracing employs a three-dimensional surface model representing each component of the pair of components, and the ray tracing employs parallel rays extending between three-dimensional surface models of the pair of components of the configuration.

10. The radiation therapy simulation or planning device of claim 9, further comprising:
a display; and
at least one user input device;
wherein the updating the generated configurations of components to eliminate the identified collision comprises:
displaying, on the display, a three-dimensional rendering of a configuration of the generated configurations of components containing an identified collision including displaying three-dimensional renderings of the three-dimensional surface models representing the pair of components; and
receiving at least one of an updated configuration and an updated margin for the pair of components of the identified collision via the at least one user input device.

11. The radiation therapy simulation or planning device of claim 9, wherein the operations further include:
generating a radiation therapy delivery plan comprising radiation delivery settings at control points chosen from the generated configurations of components.

12. The radiation therapy simulation or planning device of claim 11, wherein the generating the configurations of components includes:
generating the configurations of components for a radiation therapy delivery simulation performed prior to radiation therapy planning.

13. The radiation therapy simulation or planning device of claim 9, wherein the generating configurations of components includes importing a pre-calculated set of configurations of components, and the operations further include:
displaying to a user a set of identified collisions for the imported pre-calculated set of configurations of components for a current location of known pieces of a configuration.

14. A radiation therapy device comprising:
a radiation therapy simulation or planning device of claim 11; and
a radiation delivery device;
wherein the radiation delivery device is operative to deliver a continuous-arc radiation therapy to a patient in accordance with the generated radiation therapy delivery plan, in which the radiation delivery device applies a therapeutic radiation to the patient during a traversal of an arc between successive control points of a sequence of control points.

15. A radiation therapy device comprising:
a radiation therapy simulation or planning device of claim 11; and
a radiation delivery device;
wherein the radiation delivery device is operative to deliver a stepwise radiation therapy to a patient in accordance with the generated radiation therapy delivery plan, in which the radiation delivery device applies a therapeutic radiation to the patient at successive control points of a sequence of control points, and the radiation delivery device does not apply a therapeutic radiation to the patient during a traversal between successive control points of the sequence of control points.

16. A radiation therapy simulation or planning method comprising:

generating a radiation therapy delivery plan comprising radiation delivery settings at a plurality of control points using a computer to optimize the radiation delivery settings respective to a set of dose objectives, wherein each control point of the plurality of control points is defined by a configuration of components including at least a radiation delivery device and a patient wherein the configuration of components defines positions of the components in a common coordinate system;

for a configuration of components of each control point of the plurality of control points and for each configuration of components of a plurality of configurations between the plurality of control points traversed during an execution of the radiation therapy delivery plan, computing, using ray tracing, proximities of pairs of components of the configuration of components using three-dimensional surface models representing the pair of components, and identifying a collision of the pair of components having a computed proximity that is less than a margin for the pair of components, wherein the computing proximities of pair of components and the identifying a collision of the pair of components are performed by the computer; and displaying, on a display, the identified collision of the pair of components.

17. The radiation therapy simulation or planning method of claim 16, wherein the computing, using ray tracing, proximities of pairs of components of the configuration of components comprises:

computing proximities of pairs of components of the configuration of components by performing ray tracing between the three-dimensional surface models representing the pair of components.

18. The radiation therapy simulation or planning method of claim 17, wherein the computing, using ray tracing, proximities of pairs of components of the configuration of components comprises:

computing lengths of parallel rays extending between the three-dimensional surface models of the pair of components; and selecting a proximity having a shortest computed length of the parallel rays as the computed proximity.

19. The radiation therapy simulation or planning method of claim 16, wherein the displaying, on the display, the identified collision of the pair of components comprises:

displaying, on the display, a three-dimensional rendering of a configuration of components containing the identified collision of the pair of components including displaying three-dimensional renderings of the three-dimensional surface models representing the pair of components; and displaying an indication of the identified collision of the pair of components in the three-dimensional rendering of the configuration of components containing the identified collision of the pair of components.

* * * * *